(12) United States Patent
King et al.

(10) Patent No.: US 9,878,039 B1
(45) Date of Patent: Jan. 30, 2018

(54) MICROCAPSULE HAVING A MICROCAPSULE SHELL MATERIAL THAT IS RUPTURABLE VIA A RETRO-DIMERIZATION REACTION

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/253,967

(22) Filed: Sep. 1, 2016

(51) Int. Cl.
| | | |
|---|---|---|
| *A61K 9/50* | (2006.01) | |
| *A61K 41/00* | (2006.01) | |
| *A01N 25/28* | (2006.01) | |
| *A01N 25/10* | (2006.01) | |
| *A61K 47/10* | (2017.01) | |
| *A61K 8/06* | (2006.01) | |
| *A61K 8/34* | (2006.01) | |
| *A61Q 13/00* | (2006.01) | |

(52) U.S. Cl.
CPC .......... *A61K 41/0028* (2013.01); *A01N 25/10* (2013.01); *A01N 25/28* (2013.01); *A61K 8/062* (2013.01); *A61K 8/347* (2013.01); *A61K 9/5089* (2013.01); *A61K 47/10* (2013.01); *A61Q 13/00* (2013.01); *A61K 2800/612* (2013.01); *A61K 2800/81* (2013.01)

(58) Field of Classification Search
CPC .............. A61K 9/5089; A61K 2800/81; A61K 41/0028
USPC ..................... 424/445; 514/27, 283, 449
See application file for complete search history.

(56) References Cited

U.S. PATENT DOCUMENTS

| | | |
|---|---|---|
| 3,585,982 A | 6/1971 | Hollinshead |
| 3,653,372 A | 4/1972 | Douglas |
| 4,095,583 A | 6/1978 | Petersen et al. |
| 5,904,796 A | 5/1999 | Freuler et al. |
| 5,984,995 A | 11/1999 | White |
| 6,114,413 A | 9/2000 | Kang et al. |
| 6,518,330 B2 | 2/2003 | White et al. |
| 6,947,285 B2 | 9/2005 | Chen et al. |
| 7,290,549 B2 | 11/2007 | Banerjee et al. |
| 7,816,785 B2 | 10/2010 | Iruvanti et al. |
| 7,834,442 B2 | 11/2010 | Furman et al. |
| 7,886,813 B2 | 2/2011 | Hua et al. |
| 8,174,112 B1 | 5/2012 | Karp et al. |
| 8,206,515 B2 | 6/2012 | Nishina et al. |
| 8,518,682 B2 | 8/2013 | Freyman et al. |
| 8,741,804 B2 | 6/2014 | Boday et al. |
| 8,829,082 B2 | 9/2014 | Boday et al. |
| 8,896,110 B2 | 11/2014 | Hu et al. |
| 2006/0079021 A1 | 4/2006 | Yang |
| 2006/0228542 A1 | 10/2006 | Czubarow |
| 2008/0038540 A1 | 2/2008 | Hirayama et al. |
| 2011/0039980 A1 | 2/2011 | Caruso et al. |
| 2012/0184682 A1* | 7/2012 | Dasgupta .............. C07C 43/215 525/277 |
| 2013/0034739 A1 | 2/2013 | Boday et al. |
| 2013/0338280 A1 | 12/2013 | Boday et al. |
| 2014/0110049 A1 | 4/2014 | Yuen et al. |
| 2014/0368992 A1 | 12/2014 | Strader et al. |
| 2017/0129825 A1 | 5/2017 | Campbell et al. |
| 2017/0130102 A1 | 5/2017 | Campbell et al. |
| 2017/0130993 A1 | 5/2017 | Campbell et al. |

FOREIGN PATENT DOCUMENTS

| | | |
|---|---|---|
| CA | 918331 | 1/1973 |
| CN | 1305403 A | 7/2001 |
| CN | 1794979 A | 6/2006 |
| CN | 103626804 A | 3/2014 |
| CN | 103740978 A | 4/2014 |
| CN | 103740997 A | 4/2014 |
| CN | 103626804 B | 4/2016 |
| CN | 103976976 B | 5/2016 |
| EP | 0206620 A2 | 12/1986 |
| GB | 209479 A | 1/1924 |
| JP | 04100594 A | 4/1992 |
| JP | 08025083 A | 1/1996 |
| JP | 2000317578 A | 11/2000 |
| JP | 2001176924 A | 6/2001 |
| JP | 4073571 B2 | 2/2008 |
| KR | 1020140051091 A | 4/2014 |
| KR | 101494100 B1 | 2/2015 |
| TW | 200425250 A | 11/2004 |
| WO | WO-2009029804 A2 | 3/2009 |
| WO | WO-2011086018 A1 | 7/2011 |
| WO | WO-2014204828 A2 | 12/2014 |

OTHER PUBLICATIONS

AUS920160300US1, Appendix P; List of IBM Patent or Applications Treated as Related, May 25, 2017, 2 pages.

Long et al., *Bio-inspired controlled release through compression-relaxation cycles of microcapsules*, NPG Asia Materials (2015) 7, e148, Jan. 9, 2015, 7 pages, Springer Nature, Macmillan Publishers Limited, UK, DOI: 10.1038/am.2014.114.

Noa Lapidot et al., *Advanced Sunscreens: UV Absorbers Encapsulated in Sol-Gel Glass Microcapsules*, Journal of Sol-Gel Science and Technology, vol. 26, Issue 1, Abstract Only, <http://link.springer.com/article/10.1023/a:1020785217895>, dated Jan. 2003, 2 pages.

Tagra, *SUNCAPS, Non-breakable and transparent microcapsules containing UV filters, ideal for all cosmetic formulations*, tagra of the efal group, Tagra Biotechnologies Ltd., <http://www.in-cosmeticskorea.com/_novadocuments/237313?v=635983121662630000>, printed Nov. 1, 2016, 4 pages.

NIST, *UREA*, National Institute of Standards and Technology, Material Measurement Laboratory, <http://webbook.nist.gov/cgi/cbook.cgi?ID=C57136&Mask=400#UV-Vis-Spec>, printed Nov. 1, 2016, 2 pages.

(Continued)

*Primary Examiner* — Yanzhi Zhang

(74) *Attorney, Agent, or Firm* — Roy R. Salvagio; Steven L. Bennett; Kennedy Lenart Spraggins LLP

(57) ABSTRACT

A microcapsule encapsulates a payload agent, the microcapsule having a microcapsule shell material that is rupturable (e.g., to release the encapsulated payload agent) via a retro-dimerization reaction.

16 Claims, 4 Drawing Sheets

(56) References Cited

OTHER PUBLICATIONS

Yamaura et al., *Preparation and characterization of (3-aminopropyl) triethoxysilane-coated magnetite nanoparticles*, Journal of Magnetism and Magnetic Materials, vol. 279, Issues 2-3, Aug. 2004, pp. 210-217, ScienceDirect.com (online), Elsevier B.V., Amsterdam.
Kreft et al., *Shell-in-Shell Microcapsules: A Novel Tool for Integrated, Spatially Confined Enzymatic Reactions*, Angewandte Chemie, Int. Ed., Jul. 2007 (online Jun. 2007), vol. 46, Issue 29, pp. 5605-5608, Wiley-VCH Verlag GmbH & Co., KGaA, Weinheim, DOI: 10.1002/anie.200701173.
Xiong et al., *Towards Theranostic Multicompartment Microcapsules: in-situ Diagnostics and Laser-induced Treatment*, Theranostics, vol. 3, Issue 3, Feb. 2013, pp. 141-151, Ivyspring International, Sydney, Australia.
Marzzacco, *The Effect of a Change in the Catalyst on the Enthalpy of Decomposition of Hydrogen Peroxide*, pp. 12-13, Chem 13 News, Nov. 2008, reprinted from pp. 16-17, May 2001, University of Waterloo, Waterloo, ON, Canada.
Masin, *The Chemistry of Hand Warmers*, 3 pages, chemistryislife.com (online), accessed Jun. 5, 2017, URL: www.chemistryislife.com/the-chemistry- of-hand-warmer.
Unknown, *Flameless Chemical Heaters*, zenstoves.net (online), 4 pages, accessed Jun. 5, 2017, URL: http://zenstoves.net/Flameless.htm.
Unknown, *Flameless Ration Heater (FRH)*, MREInfo.com (online), 2014, 5 pages, accessed Jun. 5, 2017, URL: www.mreinfo.com/us/mre/frh.html.
Kawashita et al., *In vitro heat generation by ferrimagnetic maghemite microspheres for hyperthermic treatment of cancer under alternating magnetic field*, Journal of Materials Science: Materials in Medicine, vol. 19, Issue 5, pp. 1897-1903, May 2008, (Abstract Only, 2 pages), URL: www.ncbi.nlm.nih.gov/pubmed/17914614.
Unknown, *PTFE Coatings*, Specific Heat of Some Common Substances, engineeringtoolbox.com (online), 7 pages, accessed Jun. 5, 2017, URL: www.engineeringtoolbox.com/specific-heat-capacity-d_391.html.
Unknown, *Standard enthalpy change of formation (data table)*, Wikipedia.org (online), 13 pages, accessed Jun. 5, 2017, URL: en.wikipedia.org/wiki/Standard_enthalpy_change_of_formation_%28data_table%29.
Unknown, *Technical Overview: Microencapsulation*, microteklabs.com (online), 4 pages, accessed Jun. 5, 2017, URL: www.microteklabs.com/technical_overview.pdf.
Unknown, *Thermochemistry*, 7 pages, Olomouc—Hejčín Gymnasium (online), 7 pages, acessed Jun. 5, 2017, URL: http://smd.gytool.cz/downloads/thermochemistry_bar.pdf.
Delcea et al., *Multicompartmental Micro- and Nanocapsules: Hierarchy and Applications in Biosciences*, Macromolecular Bioscience, vol. 10, May 2010, pp. 465-474, Wiley-VCH Verlag GmbH & Co., Weinheim.
Lee, *Microencapsulated Heat Generating Material to Accelerate the Curing Process During Liquid Crystal Display Fabrication*, NineSigma, Inc. (online), 2014 (month unknown), 3 pages, accessed Jun. 5, 2017, URL: https://ninesights.ninesigma.com/rfps/-/rfp-portlet/rfpViewer/2690.
Keller et al., *Mechanical Properties of Microcapsules Used in a Self-Healing Polymer*, Experimental Mechanics, vol. 46, Nov. 2006, pp. 725-733, Society for Experimental Mechanics, Bethel, CT.
Hu et al., *Controlled Rupture of Magnetic Polyelectrolyte Microcapsules for Drug Delivery*, Langmuir, vol. 24, Sep. 2008, pp. 11811-11818, American Chemical Society, USA.
Unknown, *Materials for Sealing Liquid Crystal*, Three Bond Technical News, vol. 43, May 1994, pp. 1-8, Three Bond Europe, UK.
Unknown, *Advanced Technologies for LCD Assembly*, DowCorning.com (online), 2014 (month unknown), 4 pages, accessed Jun. 5, 2017, URL: www.dowcorning.com/content/publishedlit/11-3437_Advanced_Technologies_LCD_Assembly.pdf?wt.svl=ELEC_LHH.
Unknown, *Loctite Eccobond DS 6601*, Henkel.com (online), Mar. 2013, 2 pages, URL: https://tds.us.henkel.com/NA/UT/HNAUTTDS.nsf/web/C0DD8377AB27D63985257B41005DC4A1/$File/LOCTITE%20ECCOBOND%20DS%206601-EN.pdf.
Stober et al., *Controlled Growth of Monodisperse Silica Spheres in the Micron Size Range*, Journal of Colloid and Interface Science, vol. 26, Jan. 1968, pp. 62-69, Elsevier Inc., Amsterdam.
Brown, et al., "In situ poly(urea-formaldehyde) microencapsulation of dicyclopentadiene", Journal of Microencapsulation, Nov.-Dec. 2003, vol. 20, No. 6, pp. 719-730, Taylor & Francis Ltd (online, www.tandf.co.uk/journals), DOI: 10.1080/0265204031000154160.
Yuan, et al., "Photocleavable Microcapsules Built from Photoreactive Nanospheres", Langmuir, Sep. 2005, vol. 21, Issue 20, pp. 9374-9380, American Chemical Society (published on Web Aug. 2005), Washington, DC.
Alvarez-Lorenzo, et al., "Light-sensitive Intelligent Drug Delivery Systems", Photochemistry and Photobiology, Jul.-Aug. 2009, vol. 85, Issue 4, pp. 848-860, The American Society of Photobiology, John Wiley & Sons, Hoboken, NJ, DOI: 10.1111/j.1751-1097.2008.00530.x. coumarin photodimer door for microcapsule pores.pdf.
Yu, et al., "Supramolecular hydrogel microcapsules via cucurbit[8]uril host-guest interactions with triggered and UV-controlled molecular permeability", Journal, Chemical Science, Issue 6, Jun. 2015, Royal Society of Chemistry, London, UK, DOI: 10.1039/c5sc01440a.
Bogdanowicz, et al., "Preparation and Characterization of Light-Sensitive Microcapsules Based on a Liquid Crystalline Polyester", Langmuir, Feb. 2013, vol. 29, Issue 5, pp. 1601-1608, American Chemical Society (published on Web Dec. 2012), Washington, DC.

* cited by examiner

MICROCAPSULE HAVING A MICROCAPSULE SHELL MATERIAL THAT IS RUPTURABLE VIA A RETRO-DIMERIZATION REACTION

BACKGROUND

Microcapsules may be used as release systems for various types of materials (also referred to as "payloads"). Examples of payloads include perfume oils, repellants, self-healing agents, or disinfectants, among other alternatives. Rupturing the microcapsule, and release of the payload, may depend on mechanically breaking a polymer shell of the microcapsule. For example, the polymer shell may be broken by scratching, puncturing, or other mechanical means directly applied to a polymeric surface of the microcapsule.

SUMMARY

According to an embodiment, a process includes functionalizing a dimerizable molecule to form a functionalized material. The process also includes dimerizing the functionalized material to form a dimerized material with orthogonal functionality. The process further includes utilizing the dimerized material with orthogonal functionality during formation of a microcapsule that encapsulates a payload agent.

According to another embodiment, a process is disclosed that includes rupturing a microcapsule shell material of a microcapsule to release an encapsulated payload agent via a retro-dimerization reaction.

According to another embodiment, a microcapsule that encapsulates a payload agent is disclosed. The microcapsule has a microcapsule shell material that is rupturable via a retro-dimerization reaction.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

Figure 1:
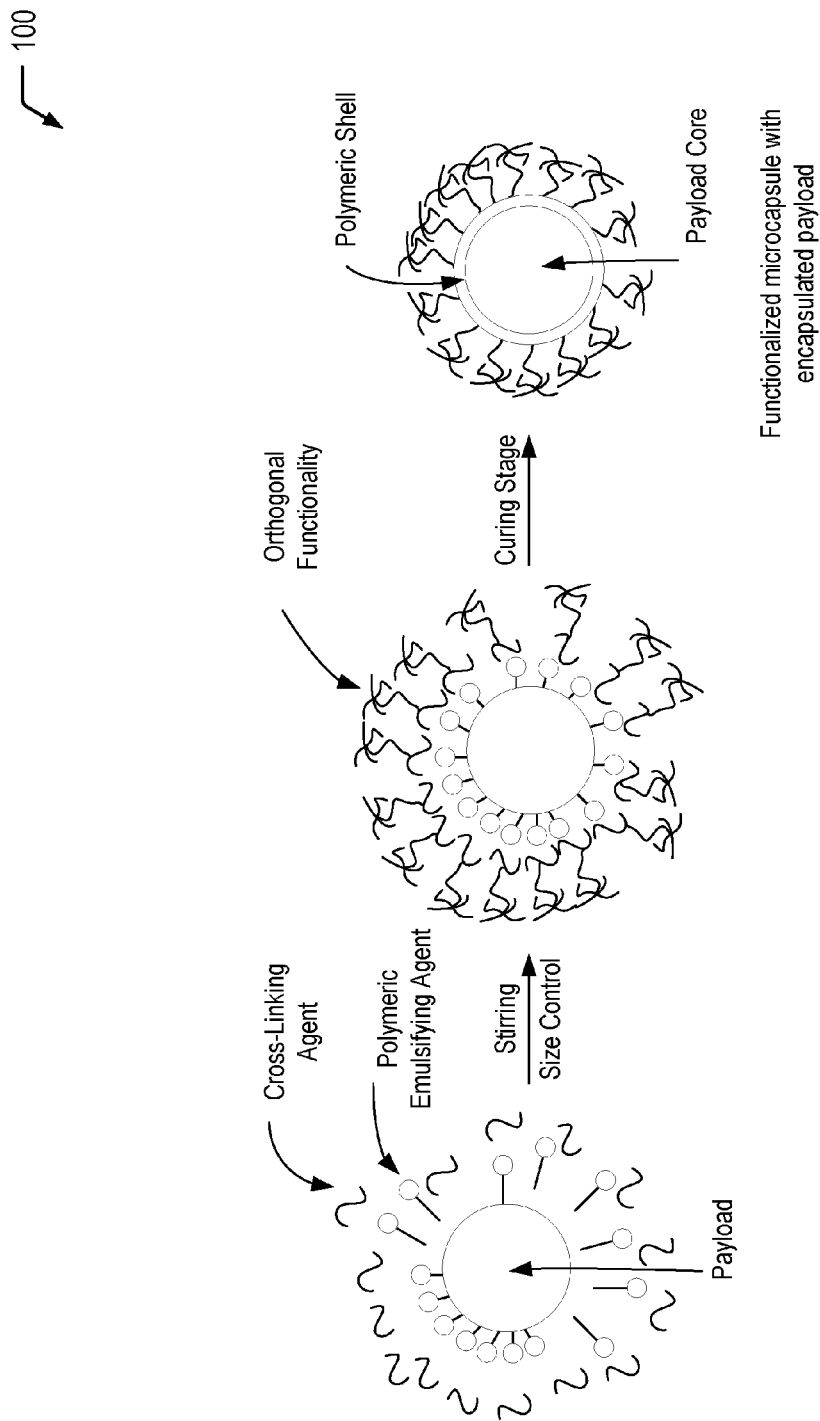
FIG. 1 is a diagram depicting a process of preparing a microcapsule (having an encapsulated payload) containing an orthogonal functionality, according to one embodiment.

The present disclosure describes processes to generate a nano/microcapsule system that releases the payload content based on retro-dimerization. Additionally, the capsules can be subjected to mechanical breaking using substantially greater mechanical force due to the microcapsule shell material disclosed herein. Further, the present disclosure describes the incorporation of orthogonal functionalities that can covalently bind into a polymer matrix, thus allowing for more sensitive detection of cracks in the polymer matrix. These nano/microcapsules can be generated with homogeneous size distributions to prevent leach out of the encapsulated payload, bind directly into a polymer matrix, and can be utilized as a functional filler to strengthen a composite material. Such microcapsules may be utilized in multiple applications.

As used herein, the term "microcapsule" is used to refer to capsules that are in a range of about 10 microns to 1000 microns in diameter. However, it will be appreciated that the following disclosure may be applied to capsules having a smaller size (also referred to as "nanocapsules"). In the present disclosure, a payload (or multiple payloads) may be incorporated into a polymeric microcapsule that is generated containing dimer blocks. Further, the dimer-containing blocks can have orthogonal functionality, affording the ability to covalently bind to a polymeric matrix. After incorporation of these microcapsules into the polymer matrix, the capsules may be ruptured via retro-dimerization. In some cases, the microcapsules may be ruptured via mechanical means to release the encapsulated payload, and the microcapsule shell material may degrade via retro-dimerization (e.g., via exposure to sunlight).

Several advantages are associated with the subject matter of the present disclosure. For example, the microcapsules of the present disclosure allow for a homogeneous distribution of payload agent(s), the incorporation of microcapsules at various volumes depending on the amount of payload agent(s) that are desired, and the ability for the microcapsules to covalently bind directly into a polymeric resin. As another example, the microcapsules of the present disclosure may be used as a flow controller and assist and/or eliminate nano-silica. The microcapsules may be generated in a homogeneous size, thus allowing for a controlled release of payload agent(s) per unit area. Further, the microcapsules may be considered environmentally friendly due to the protective packaging of the microcapsule in order to prevent leach out of the payload agent(s). As a further example, the microcapsules of the present disclosure represent functional fillers that increase mechanical properties. It will be appreciated that the advantages described above are for illustrative purposes only and other advantages may be associated with the utilization of the microcapsules of the present disclosure in various contexts.

In the present disclosure, payload-containing microcapsules containing an orthogonal functionality may be manufactured using an oil-in-water emulsion technique to create a protective polymeric shell around a payload agent core. In a particular embodiment, (orthogonal functional) resveratrol that is dimerizable replaces standard resorcinol in the microcapsule synthesis process.

To illustrate, in a process of preparing the microcapsules of the present disclosure, a dimerizable molecule undergoes bonding to generate a resorcinol-like monomer. An illustrative, non-limiting example of a dimerizable molecule includes resveratrol. One advantage associated with the use of resveratrol is that resveratrol is a naturally occurring bio-based material, thus increasing the renewable bio-based content of the associated microcapsules. Other dimerizable molecules may be selected by one of ordinary skill in the art.

A payload agent acts as the oil phase that is dispersed into an aqueous continuous phase and stirred, thus beginning the emulsion process. One example of a payload agent that could be used is a latent curing agent such as n-ethylpiperazine. Other payload agent(s) may be selected by one of ordinary skill in the art. One area of possible payloads could be polymerizable molecules such as cyclic olefins, norbornene, substituted norbornene, cyclooctadiene, substituted cyclooctadiene, lactones, acrylates, acrylic acids, styrenes, isoprene, butadiene, isocyanate functional groups with hydroxyl functional groups, and epoxies. Such agents typically require an activator such as a catalyst and/or an initiator, which can be selected by one of ordinary skill in the art. Additionally, solvents could be incorporated into the microcapsules, including aprotic solvents, protic solvents, or combinations thereof.

A cross-linking agent is then used to react with a polymeric emulsifying agent to generate the capsule wall around the payload agent(s). Particle size may be controlled by adjusting a stir speed of the reaction (e.g., the higher the stir speed, the finer the particles). Finally, a curing step is used to complete the reaction between the cross-linking agent and the polymeric emulsifying agent to form the microcapsule. The resulting microcapsules may then be incorporated into a polymer matrix, with the microcapsules covalently binding to the polymer matrix. The amount of microcapsules to be utilized may be empirically determined based on the rheology of the polymeric resins, the microcapsule particle size, and the amount that is sufficient to reach the desired payload content for release.

Figure 2:
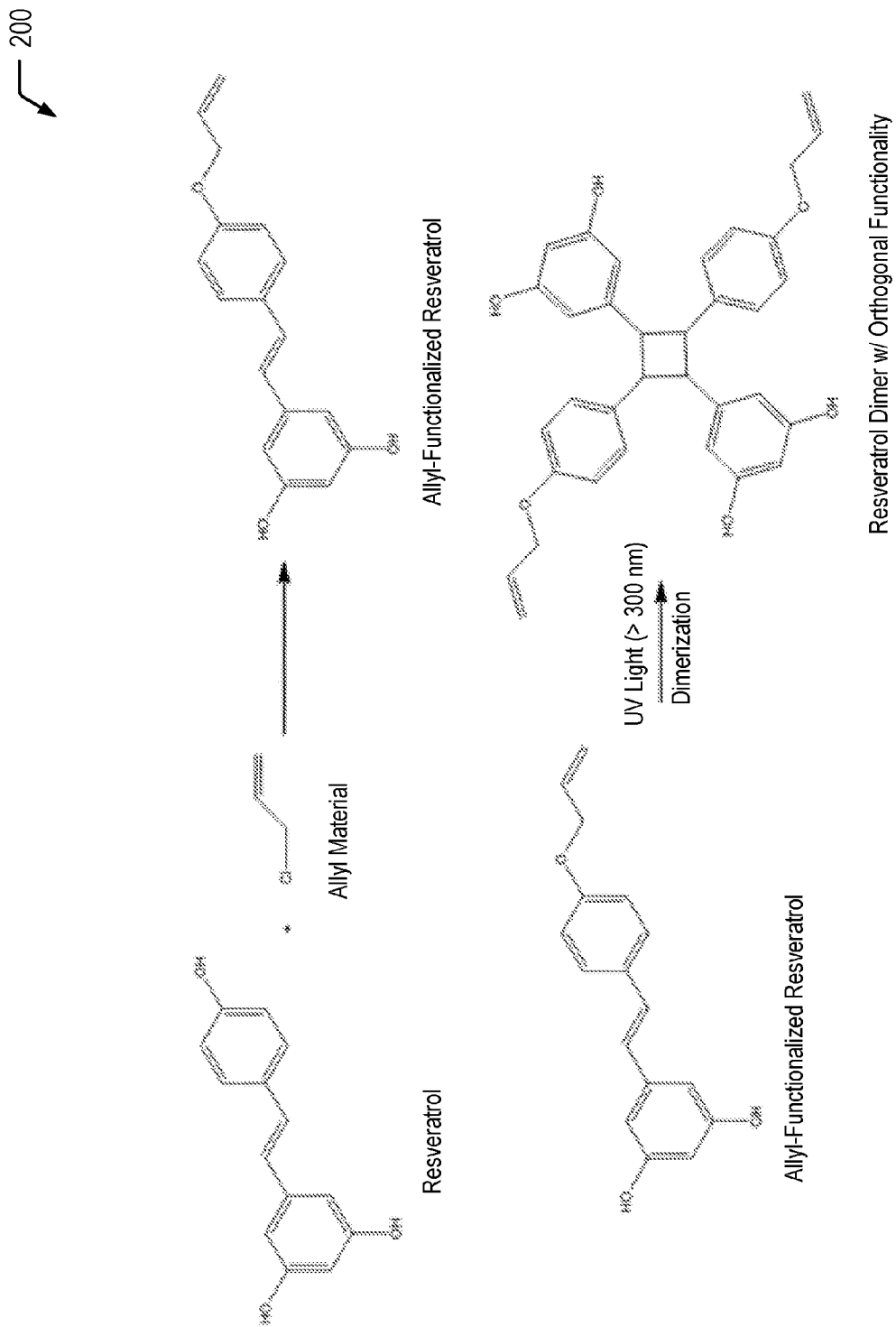
FIG. 2 is a chemical reaction diagram illustrating a process of forming a dimerized material with orthogonal functionality for use during formation of the microcapsule depicted in the example of FIG. 1, according to one embodiment.

FIG. 1 is a diagram 100 depicting an example of the preparation of a microcapsule (having an encapsulated payload) containing an orthogonal functionality. FIG. 2 depicts an example of the preparation of a resveratrol dimer with an orthogonal functionality for use in the formation of the microcapsule depicted in FIG. 1. In FIG. 1, the payload filled microcapsules containing the orthogonal functionality are formed using an oil-in-water emulsion technique to create a protective polymeric shell around a payload core. As illustrated and further described herein with respect to FIG. 3, after incorporation of the microcapsules into a polymer matrix, the microcapsules may be ruptured to release the payload via retro-dimerization of the resveratrol-containing groups.

In the example of FIG. 1, a payload represents an oil phase that is dispersed into an aqueous continuous phase and stirred to begin an emulsion process. As illustrative, non-limiting examples, the payload (or multiple payloads) may include a perfume oil, a self-healing agent, a disinfectant, a repellant, or a combination thereof. It will be appreciated that various payload(s) may be selected to provide various functionalities for various applications. In FIG. 1, a cross-linking agent is reacted with a polymeric emulsifying agent to generate a capsule wall around the payload. Particle size may be controlled by adjusting the stir speed during the reaction. For example, a faster stir speed may result in formation (on average) of smaller ("finer") particles than a slower stir speed. FIG. 1 further illustrates that a curing stage may be used to complete the reaction between the cross-linking agent and the polymeric emulsifying agent to form the microcapsules (or nanocapsules, depending on the stir speed).

In a prophetic example, the microcapsules containing an orthogonal functionality that are depicted in FIG. 1 may be prepared according to the following process. To a stirring aqueous solution containing an ethylene maleic anhydride (EMA) copolymer surfactant, urea, and $NH_4Cl$, the resveratrol dimerized reactant with an orthogonal functionality (depicted in FIG. 2) may be added. The pH may be adjusted to about 3.5 by adding NaOH and HCl (or other acids/bases), followed by the addition of an emulsifying agent. The payload may be added with other ingredients, such as monomers and/or pre-polymers, stabilizers, solvents, viscosity modifiers, odorants, colorant/dyes, blowing agents, antioxidants, or co-catalysts, or a combination thereof. Formaldehyde may be added, which acts as a curing agent to complete the shell formation. The resulting microcapsules may be subsequently washed and sieved to remove unreacted material.

Thus, FIG. 1 illustrates an example of a process of forming a microcapsule (having an encapsulated payload) containing an orthogonal functionality. As illustrated and further described herein with respect to FIG. 2, a resveratrol dimer with an orthogonal functionality may be utilized in the formation of the microcapsule depicted in FIG. 1. Additionally, as illustrated and described further herein with respect to FIG. 3, retro-dimerization of the resveratrol-containing groups (utilizing UV light) may result in rupture of the microcapsules and the associated release of the encapsulated payload agent(s). Further, in some cases, the microcapsules may be ruptured via mechanical means to release the encapsulated payload, and the microcapsule shell material may degrade via retro-dimerization (e.g., via exposure to sunlight).

Referring to FIG. 2, a chemical reaction diagram 200 depicts an example of a process of preparing a resveratrol dimer with orthogonal functionality, according to one embodiment. In the particular embodiment depicted in FIG. 2, an allyl-functionalized resveratrol is illustrated. It will be appreciated that the allyl-functionalized resveratrol depicted in FIG. 2 represents a non-limiting, illustrative example of a material with an orthogonal functionality for incorporation into the microcapsule depicted in FIG. 1. Other examples may include vinyl-functionalized resveratrol (via vinyl chloride), (meth)acrylate-functionalized resveratrol (via (meth) acryloyl chloride), and epoxy-functionalized resveratrol (via epichlorohydrin) which can be used to react with the appropriate moiety in the polymeric resin.

In the first chemical reaction depicted at the top of FIG. 2, resveratrol is chemically reacted with an allyl material to form an allyl-functionalized resveratrol. As a prophetic example, the first chemical reaction may be performed in the presence of triethylamine and tetrahydrofuran (THF) at a reaction temperature of about 0° C.

The second chemical reaction depicted at the bottom of FIG. 2 illustrates the dimerization of the allyl-functionalized resveratrol formed in the first chemical reaction using ultraviolet light (e.g., at a wavelength of at least 300 nm), resulting in a resveratrol dimer with an orthogonal functionality. The butene ring formation in the example depicted in FIG. 2 may generate a rigid molecule that may improve the strength of a standard resorcinol-containing shell.

Thus, FIG. 2 illustrates a particular embodiment of a process of producing a dimerized material with an orthogonal functionality. As further described herein, the dimerized material depicted in FIG. 2 may be utilized during the formation of the microcapsule (having an encapsulated payload), as illustrated in FIG. 1.

Figure 3:
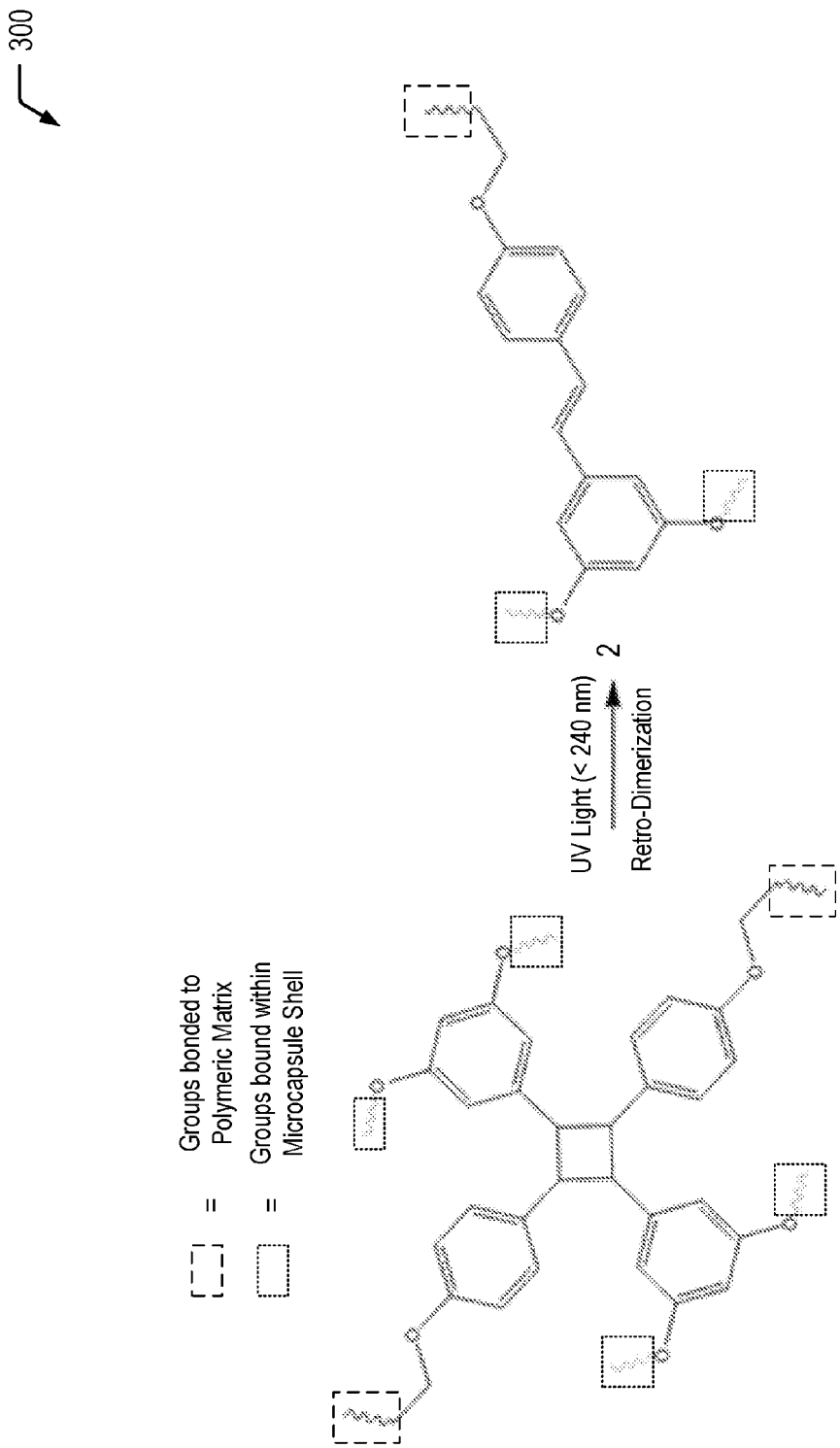
FIG. 3 is a chemical reaction diagram illustrating a process of retro-dimerization that results in rupture of the microcapsule shell material and associated release of the encapsulated payload agent(s), according to one embodiment.

Referring to FIG. 3, a chemical reaction diagram 300 depicts an example of a process of retro-dimerization that results in rupture of the microcapsule shell material and associated release of the encapsulated payload agent(s). Alternatively, the microcapsules may be ruptured via mechanical means to release the encapsulated payload, and the microcapsule shell material may degrade via retro-dimerization (e.g., via exposure to sunlight).

The left side of the chemical reaction diagram depicted in FIG. 3 illustrates that incorporation of the microcapsule with the orthogonal functionality depicted in FIG. 1 into a polymeric matrix material, a first portion of the orthogonal groups are bound within the microcapsule shell and a second portion of the orthogonal groups are bound to the polymeric matrix material.

The right side of the chemical reaction diagram depicted in FIG. 3 illustrates that UV light (e.g., at a wavelength that is less than 240 nm) results in a retro-dimerization reaction. The retro-dimerization of the resveratrol-containing groups may result in rupture of the microcapsules and the associated release of the encapsulated payload agent(s). In other cases, the microcapsules may be ruptured via mechanical means to release the encapsulated payload, and the microcapsule shell material may degrade via retro-dimerization (e.g., via exposure to sunlight).

Thus, FIG. 3 illustrates an example of a retro-dimerization reaction that is initiated via UV light that may result in the rupture of the microcapsules and the associated release of the encapsulated payload agent(s). Alternatively, as described herein, in some cases, the microcapsules may be ruptured via mechanical means to deliver the encapsulated payload, and the retro-dimerization reaction may degrade the microcapsule shell material. In some cases, the UV light may be from a natural source (e.g., sunlight), while in other cases an end user may apply UV light in order to initiate the rupture of the microcapsule shell material.

Figure 4:
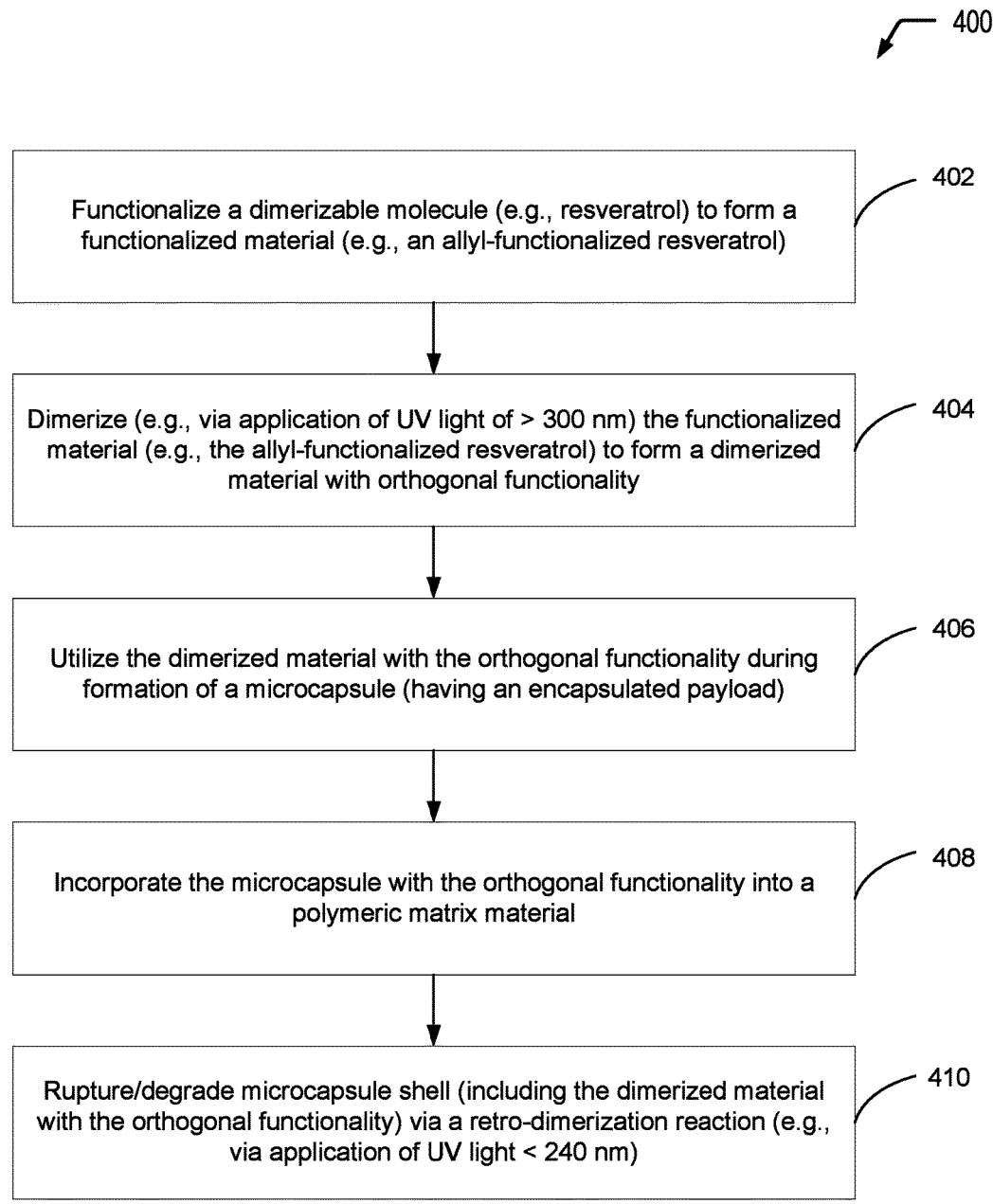
FIG. 4 is a flow diagram showing a particular embodiment of a process of forming a polymeric material that includes microcapsules with encapsulated payload agent(s) that may be released via a retro-dimerization reaction.

Referring to FIG. 4, a flow diagram depicts an example of a process 400 of forming a polymeric material that includes a microcapsule (having an encapsulated payload) having orthogonal functionality that is bonded to the polymeric material. In the particular embodiment depicted in FIG. 4, the process 400 further includes rupturing the microcapsule shell material via retro-dimerization to release the encapsulated payload agent(s). FIG. 4 illustrates an example of a process of producing a microcapsule that includes orthogonal functional groups (as shown in FIG. 1 and further described herein with respect to FIG. 2). FIG. 4 further illustrates that the microcapsule having the orthogonal functionality may be blended with or applied to the polymeric material, and the microcapsule may be bonded to the polymeric material via a chemical reaction of a portion of the orthogonal functional groups of the dimerized material (as illustrated and further described herein with respect to FIG. 3). As described further herein with respect to FIG. 3, the microcapsules that are bonded to the polymeric material may be ruptured via retro-dimerization when exposed to UV light.

In the particular embodiment illustrated in FIG. 4, operations associated with an example process of producing microcapsules containing orthogonal functionality are identified as operations 402-406, while operations associated with incorporating the microcapsules into a polymeric matrix material are illustrated as operation 408, and operations associated with rupturing the microcapsules are illustrated as operation 410. It will be appreciated that the operations shown in FIG. 4 are for illustrative purposes only and that the operations may be performed in alternative orders, at alternative times, by a single entity or by multiple entities, or a combination thereof. As an example, one entity may produce the allyl-functionalized resveratrol depicted in FIG. 2, another entity may utilize the allyl-functionalized resveratrol to form the resveratrol dimer with the orthogonal functionality depicted in FIG. 2, while another entity may produce the microcapsule containing the orthogonal functionality depicted in FIG. 1. Further, alternative or additional entities may perform the operations associated with bonding the microcapsule depicted in FIG. 1 to the polymeric matrix material. Additionally, another entity (or naturally in the environment as a result of exposure to sunlight) may rupture the microcapsule shell to release the encapsulated payload(s) and/or to degrade the microcapsule shell after rupture via mechanical means.

The process 400 includes functionalizing a dimerizable molecule to form a functionalized material, at 402. For example, referring to the first chemical reaction depicted at the top of FIG. 2, resveratrol may be chemically reacted with an allyl material to form an allyl-functionalized resveratrol. It will be appreciated that resveratrol is one example of a dimerizable molecule that undergoes bonding to generate a resorcinol-like monomer and that other dimerizable materials may be utilized in other embodiments. Further, the allyl-functionalized resveratrol depicted in FIG. 2 represents a non-limiting, illustrative example of a material with an orthogonal functionality for incorporation into the microcapsule depicted in FIG. 1. Other examples may include vinyl-functionalized resveratrol (via vinyl chloride), (meth) acrylate-functionalized resveratrol (via methacryloyl chloride), and epoxy-functionalized resveratrol (via epichlorohydrin) which can be used to react with the appropriate moiety in the polymeric resin.

The process 400 includes dimerizing the functionalized material to form a dimerized material with orthogonal functionality, at 404. For example, the second chemical reaction depicted at the bottom of FIG. 2 illustrates the dimerization of the allyl-functionalized resveratrol formed in the first chemical reaction using ultraviolet light (e.g., at a wavelength of at least 300 nm), resulting in a resveratrol dimer with an orthogonal functionality.

The process 400 includes utilizing the dimerized material with the orthogonal functionality during formation of a microcapsule (having an encapsulated payload), at 406. For example, resveratrol dimer with the orthogonal functionality depicted in FIG. 2 may be utilized during the process of forming the microcapsules (having the encapsulated payload) depicted in FIG. 1. As described further herein, the payload filled microcapsules containing the orthogonal functionality depicted in FIG. 1 may be formed using an oil-in-water emulsion technique to create a protective polymeric shell around a payload core.

In the particular embodiment depicted in FIG. 4, the process 400 also includes incorporating the microcapsule with the orthogonal functionality into a polymeric matrix material, at 408. For example, referring to the left side of the chemical reaction diagram depicted in FIG. 3, a first portion of the orthogonal groups of the dimerized resveratrol material of FIG. 2 may be bound within the microcapsule shell and a second portion of the orthogonal groups may be bonded to the polymeric matrix material.

In the particular embodiment depicted in FIG. 4, the process 400 also includes rupturing the microcapsule shell (including the dimerized material with the orthogonal functionality) via a retro-dimerization reaction, at 410. For example, as illustrated and further described herein with respect to FIG. 3, retro-dimerization (e.g., via application of UV light at a wavelength <240 nm) may result in rupture of the microcapsule shell material and associated release of the encapsulated payload. Alternatively, as described further herein, in some cases, the microcapsule shell may rupture via mechanical means, and exposure to UV light (e.g., sunlight) may result in degradation of the remaining microcapsule shell material.

Thus, FIG. 4 illustrates an example of a process of forming a polymeric material that includes a microcapsule (having an encapsulated payload) having orthogonal functionality that is bonded to the polymeric material. FIG. 4 further illustrates that the microcapsules that are bonded to the polymeric material may be ruptured (or subsequently degraded after mechanical rupture) via retro-dimerization when exposed to UV light.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process comprising: functionalizing a resveratrol molecule to form a functionalized material;
   dimerizing the functionalized material to form a resveratrol dimer with an orthogonal functionality, the orthogonal functionality including an allyl group, a vinyl group, a (meth)acrylate group, or an epoxy group; and
   utilizing the resveratrol dimer with the orthogonal functionality during formation of a microcapsule that encapsulates a payload agent.

2. The process of claim 1, wherein dimerizing the functionalized material includes applying ultraviolet (UV) light having a wavelength that is greater than 300 nm.

3. The process of claim 1, wherein the payload agent includes a perfume oil, a repellant, a self-healing agent, or a disinfectant.

4. The process of claim 1, further comprising incorporating the microcapsule into a polymeric matrix material.

5. A process comprising rupturing a microcapsule shell material of a microcapsule to release an encapsulated payload agent via a retro-dimerization reaction, wherein the microcapsule shell material includes a resveratrol dimer with an orthogonal functionality, the orthogonal functionality including an allyl group, a vinyl group, a (meth)acrylate group, or an epoxy group.

6. The process of claim 5, wherein the retro-dimerization reaction is initiated via application of ultraviolet (UV) light having a wavelength that is less than 240 nm.

7. The process of claim 6, wherein the UV light includes sunlight.

8. The process of claim 5, wherein the encapsulated payload agent includes a perfume oil, a repellant, a self-healing agent, or a disinfectant.

9. The process of claim 5, wherein the microcapsule is incorporated into a polymeric matrix material.

10. A microcapsule that encapsulates a payload agent, the microcapsule having a microcapsule shell material that is rupturable via a retro-dimerization reaction, wherein the microcapsule shell material includes a resveratrol dimer with an orthogonal functionality, the orthogonal functionality including an allyl group, a vinyl group, a (meth)acrylate group, or an epoxy group.

11. The microcapsule of claim 10, wherein the retro-dimerization reaction is initiated via application of ultraviolet (UV) light having a wavelength that is less than 240 nm.

12. The microcapsule of claim 10, wherein the encapsulated payload agent includes a perfume oil, a repellant, a self-healing agent, or a disinfectant.

13. The process of claim 1, wherein the functionalized material includes an allyl-functionalized resveratrol material having the following chemical structure:

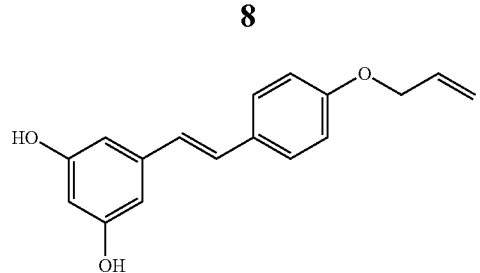

14. The process of claim 13, wherein the resveratrol dimer with the orthogonal functionality has the following chemical structure:

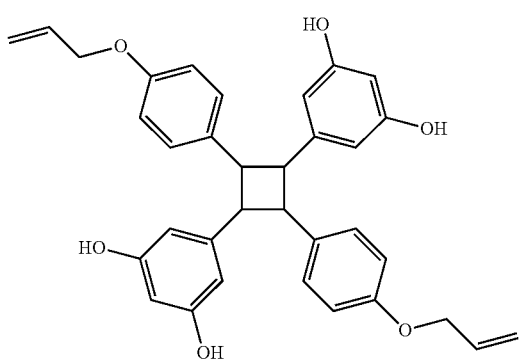

15. The process of claim 5, wherein the resveratrol dimer with the orthogonal functionality has the following chemical structure:

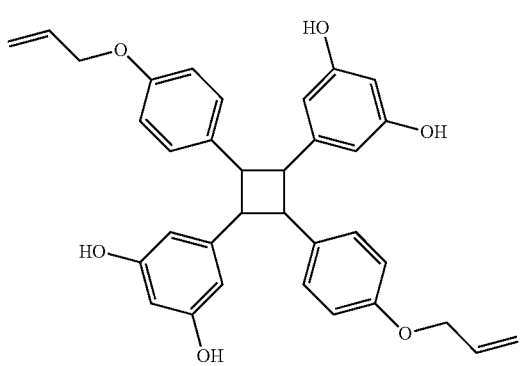 [SMILES: C=CCOc1ccc(C2C(c3cc(O)cc(O)c3)C(c3ccc(OCC=C)cc3)C2c2cc(O)cc(O)c2)cc1]

16. The microcapsule of claim 10, wherein the resveratrol dimer with the orthogonal functionality has the following chemical structure:

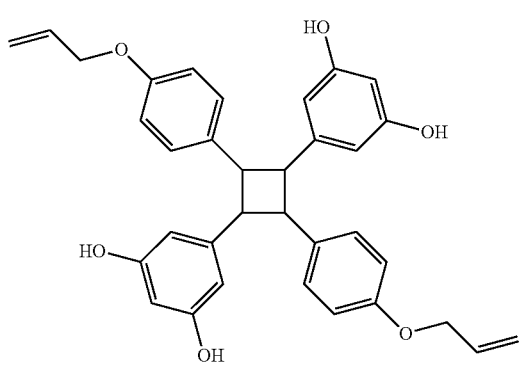

* * * * *